US00RE37045E

(19) United States

(12) Reissued Patent

Olsson et al.

(10) Patent Number: US RE37,045 E

(45) Date of Reissued Patent: Feb. 6, 2001

(54) N-6 SUBSTITUTED-5'-(N-SUBSTITUTED CARBOXAMIDE)ADENOSINES AS CARDIAC VASODILATOR AND ANTIHYPERTENSIVE AGENTS

(75) Inventors: Ray A. Olsson, Tampa, FL (US); Robert D. Thompson, Manchester, NH (US)

(73) Assignee: Discovery Therapeutics, Inc., Richmond, VA (US)

(21) Appl. No.: 09/234,501

(22) Filed: Jan. 21, 1999

Related U.S. Patent Documents

Reissue of:

(64) Patent No.: 5,310,731
Issued: May 10, 1994
Appl. No.: 06/742,565
Filed: Jun. 12, 1985

U.S. Applications:

(63) Continuation-in-part of application No. 06/625,450, filed on Jun. 28, 1984, now abandoned.

(51) Int. Cl.[7] ..... A61K 31/70; C07H 19/167

(52) U.S. Cl. ..... 514/46; 514/45; 536/27.22

(58) Field of Search ..... 514/46, 45; 536/27.22

(56) References Cited

U.S. PATENT DOCUMENTS

| | | | | |
|---|---|---|---|---|
| 3,502,649 | | 3/1970 | Thiel et al. | 536/27.62 |
| 3,509,129 | | 4/1970 | Kampe et al. | 536/27.62 |
| 3,590,029 | | 6/1971 | Koch et al. | 536/27.61 |
| 3,781,273 | * | 12/1973 | Kampe et al. | 536/27.62 |
| 3,851,056 | | 11/1974 | Stork et al. | 514/46 |
| 3,901,876 | | 8/1975 | Vorbrüggen et al. | 536/27.62 |
| 3,931,401 | | 1/1976 | Prasad et al. | 514/43 |
| 3,966,916 | | 6/1976 | Kampe et al. | 514/46 |
| 4,029,884 | | 6/1977 | Stein et al. | 536/27.22 |
| 4,090,021 | | 5/1978 | Vorbrüggen | 536/26.71 |
| 4,167,565 | | 9/1979 | Stein et al. | 514/46 |
| 4,224,438 | | 9/1980 | Fauland et al. | 536/27.22 |
| 4,514,405 | | 4/1985 | Irmscher et al. | 514/46 |

FOREIGN PATENT DOCUMENTS

| | | |
|---|---|---|
| 2 007 273 | 8/1971 | (DE) . |
| 58-167599 | 10/1983 | (JP) . |
| 67/7630 | 4/1968 | (ZA) . |

OTHER PUBLICATIONS

Daly, J.W., "Adenosine Receptors: Targets for Future Drugs," *J. Med. Chem. 25*:197–207 (Mar. 1982).

Daly, J.W. et al., "Structure–Activity Relationships for $N^6$–Substituted Adenosines at a Brain $A_1$–Adenosine Receptor with a Comparison to an $A_2$–Adenosine Receptor Regulating Coronary Blood Flow," *Biochem. Pharmacol. 35*:2467–2481 (Aug. 1986).

Fleysher, M.H. et al., "Synthesis and biological activity of some new $N^6$–substituted purine nucloesides," *Chem. Abstracts 72*:349, Abstract No. 3706g, (Jan. 1970).

(List continued on next page.)

*Primary Examiner*—Gary Geist
*Assistant Examiner*—L. Eric Crane
(74) *Attorney, Agent, or Firm*—Sterne, Kessler, Goldstein & Fox P.L.L.C.

(57) ABSTRACT

Compounds of the formula

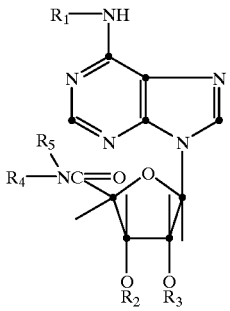

are disclosed, wherein $R_1$, represents secondary alkyl; aralkyl; cycloalkyl; heteroaryl substituted alkyl; norbornyl; and substituted secondary alkyl, aralkyl, cycloalkyl, heteroaryl substituted alkyl, norbornyl; and para-substituted phenyl groups; and $R_2$ and $R_3$ are hydrogen or pharmacologically acceptable acyl groups. The compounds of the invention are useful as cardiovascular vasodilator or antihypertensive agents. The therapeutically useful compounds of the invention as well as similar 5-N and N-6 substituted adenosine 5-uronamides are prepared, in accordance with a novel process, from isopropylidene (or otherwise suitably blocked) inosine-5'-uronic acid. Isopropylideneinosine-5'-uronic acid is reacted with a suitable inorganic acid halide, such as thionyl chloride, to yield 6-halogeno-9-[2',3'-O-isopropylidene-β-D-ribofuranosyl-5-uronic acid halide]-9H-purine. This intermediate is reacted with an amine of the general formula $R_4R_5NH$ to give a 6-halogeno substituted, substituted uronic acid amide of the formula

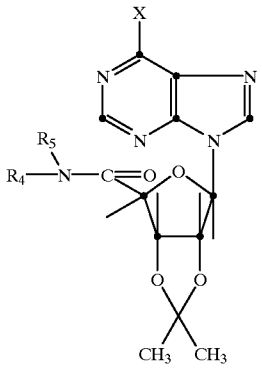

wherein X is halogen. Reaction of the latter intermediate with an amine of the formula $R_1$—$NH_2$, and removal of the isopropylidene (or other) blocking groups yields the compounds of the invention.

35 Claims, No Drawings

OTHER PUBLICATIONS

Fox, I.H. and L. Kurpis, "Binding Characteristics of an Adenosine Receptor in Human Placenta," *J. Biol. Chem. 258*:6952–6955 (Jun. 1983).

Goodman, L., "Chemical Syntheses and Transformations of Nucleosides," in: *Basic Principles in Nucleic Acid Chemistry,* Ts'O, P.O.P., ed., Academic Press, New York, publ., pp. 150–151 (1974).

Olsson, R.A. et al., "Use of Structure–Activity Relationships in the Study of Adenosine Receptors," in: *Methods of Pharmacology,* pp. 293–304 (1985).

Schmidt, R.R. and H.–J. Fritz, "Synthesis and Structure of Inosine–5'–carboxylic Acid and Derivatives," *Chem. Ber. 103*:1867–1871 (1970).

Schwabe, U., "General Aspects of Binding of Ligands to Adenosine Receptors," in: *Regulatory Function of Adenosine,* Berne, R.M. et al., eds., Martinus Nijhoff, Boston, publ., pp. 77–96 (1983).

Stein, H.H., "Ethyl–Adenosine–5'–carboxylate. A Potent Vasoactive Agent in the Dog," *J. Med. Chem. 16*:1306–1309 (Nov. 1973).

Stein, H.H. and P. Somani, "Cardiovascular Effects of Nucleoside Analogs," *Annals NY Acad. Sci. 255*:380–389 (1975).

English Language Abstract of DE 2 007 273, Derwent World Patents Index (Dialog File 351), WPI Accession No. 71–56157S. Abstract of reference AL1 herein, published Aug. 26, 1971.

Schuske, U., In Berne et al, Ch 6 of "Regulatory Function of Adenosine" (London) (Pub) pp. 77–96, 1983, Martinus Nishoff.*

* cited by examiner

N-6 SUBSTITUTED-5'-(N-SUBSTITUTED CARBOXAMIDE)ADENOSINES AS CARDIAC VASODILATOR AND ANTIHYPERTENSIVE AGENTS

Matter enclosed in heavy brackets [ ] appears in the original patent but forms no part of this reissue specification; matter printed in italics indicates the additions made by reissue.

BACKGROUND OF THE INVENTION

1. Cross-reference to Related Application

The present application is *a reissue of a U.S. Pat. No. 5,310,731, issued on May 10, 1994, which was* a continuation-in-part of application Ser. No. 625,450 filed on Jun. 28, 1984, now abandoned by the same inventors, and assigned to the same assignee as the present application.

2. Field of the Invention

The present invention is directed to certain N-6 and 5'-N substituted carboxamidoadenosine derivatives which have beneficial cardiovascular and antihypertensive activity in mammals, including humans and domestic animals. The present invention is also directed to a process for making said compounds.

3. Brief Description of the Prior Art

Adenosine has been known for a long time to possess certain cardiovascular activity and particularly coronary dilatory activity. In an effort to obtain adenosine analogs of greater potency, or longer duration of activity, or both, many analogs of this naturally occurring nucleoside have been synthesized and tested.

Moreover, numerous studies have been conducted in order to elucidate the biochemical mechanism of action of adenosine and its analogs, and several theories and hypotheses have been proposed regarding biochemical pathways and receptor sites.

For discussion of current theories regarding the foregoing, reference is made to the following articles and publications: Adenosine Receptors: Targets for Future Drugs, by John W. Daly, Journal of Medicinal Chemistry, 25, 197 (1982); Cardiovascular Effects of Nucleoside Analogs, by Herman H. Stein and Pitambar Somani, Annals New York Academy of Sciences, 255, 380 (1979); Coronary Dilatory Action of Adenosine Analogs: a Comparative Study, by G. Reberger, W. Schutz and O. Kraupp, Archives internationales de Pharmacodynamie et de Therapie 230, 140–149 (1977); Chapter 6 of the book titled: Regulatory Function of Adenosine, (pages 77–96), R. M. Berne, T. W. Rall and R. Rubio editors, Martinus Nijhoff publishers, The Hague/Boston/London; Ethyl Adenosine-5'-carboxylate: A Potent Vasoactive Agent in the Dog, by Herman H. Stein, Journal of Medicinal Chemistry, 16, 1306 (1973); Modification of the 5' Position of Purine Nucleosides: 2. Synthesis and Some Cardiovascular Properties of Adenosine-5'-(N-substituted) carboxamides, by Raj N. Prasad et al., Journal of Medicinal Chemistry, 23, 313 (1980); and Modification of the 5' Position of Purine Nucleosides: 1. Synthesis and Biological Properties of Alkyl Adenosine-5'-carboxylates by Raj N. Prasad et al., Journal of Medicinal Chemistry, 19, 1180 (1976).

In addition to the foregoing publications, German Offenlegungschrift Nos. 2133273, 2426682, 1795761, 1913818, 2007273, 2238923, 2060189, 2244328, 1814711, 2136624, South African Patent Application No. 677630 (filed on Dec. 20, 1967) and British Patent Specification No. 1,123,245 describe adenosine derivatives which have cardiovascular, coronary dilator or antilipolytic activities. Still more adenosine derivatives having beneficial cardiovascular activity are described in another application for U.S. Letters Patent of the present inventors, Ser. No. 601,435, filed on Apr. 18, 1984.

Still further, Published Japanese Patent Application Nos. 58-167599 and 58-167600 disclose adenosine 5'-carboxamide derivatives which have fibrinolysis accelerating activity. U.S. Pat. No. 4,029,334 discloses antihypertensive and anti-anginal adenosine 5'-carboxamide derivatives where the $N^6$ amino group is unsubstituted. U.S. Pat. No. 4,167,565 discloses adenosine 5'-carboxamide derivatives which have substituents both in the $N^6$ and 5'-carboxamido position, and which are useful as poisons for certain noxious animals, such as rodents and coyotes.

In the cardiovascular and anti-hypertensive field, however, the therapeutic utility of the natural nucleoside adenosine and many of its analogs is limited because the desired beneficial effect is often of relatively short duration.

More particularly, the short duration of the beneficial cardiovascular effects of adenosine and those of its analogs which have an unsubstituted hydroxyl group at C-5 of the ribofuranose moiety is usually attributed to rapid penetration into cells followed by enzymatic conversion into less active or impermeant metabolites. For example, adenosine deaminase converts adenosine into inosine, which is a weak cardiovascular agonist. Alternatively, phosphorylation, catalyzed by adenosine kinase, forms adenylic acid (5'-AMP). Ionization of the phosphate group under physiological conditions prevents the escape of 5'-AMP from the cells in which it is formed. Thus trapped, 5'-AMP cannot exert its cardiovascular actions, which are mediated by cell surface receptors, as is discussed below.

Some known adenosine analogs, however, cannot be phosphorylated in the 5' position because the 5' position is effectively blocked. 5'-N-Ethylcarboxamidoadenosine [NECA] (Compound 1 in General Formula 1) is an example of such an adenosine analog incapable of phosphorylation by adenosine kinase. Nevertheless, this compound binds potently to certain adenosine receptor sites and exhibits substantial cardiovascular activity. Other examples of known derivatives of adenosine-5'-carboxamide, (Compound 2) and of adenosine-5'-carboxylic acid (Compound 9) are shown below in General Formulae 1 and 2. Generally speaking, in these compounds, the 5'-carboxylate or 5'-carboxamide group of the uronic acid moiety is substituted with lower alkyl or lower acyl groups. Some of the adenosine-5'-carboxamide derivatives shown in General Formula 1 are disclosed in Chemical Abstracts Volume 100, 68652c and 68653d (1984) and in the corresponding Published Japanese Patent Application Nos. 58-167599 and 58-167600.

The biological activity of adenosine-5'-carboxamide derivatives, such as NECA, is thought to be due to the activation of adenylate cyclase through cell surface "$R_a$" or "$A_2$" receptors. Structure-activity studies show that the $R_a$ receptor recognizes the alkyl uronamide moiety of NECA and its congeners. A second type of cell surface adenosine receptor designated "$R_i$" or "$A_1$" inhibits the catalytic activity of adenylate cyclase. Adenosine analogs possessing certain N-6 alkyl or aralkyl substituents such as cyclohexyl or R-1-phenyl-2-propyl are selective agonists at $R_i$ receptors. Many mammalian and human cells contain both $R_a$ and $R_i$ receptors; examples of exceptions are fat cells which contain $R_i$ receptors only, and blood platelets and human placenta, in which $R_a$ receptors predominate.

Currently available agonists are only selective, not absolutely specific, for $R_a$ and $R_i$ receptors. Because the two types of receptors coexist in many organs, including brain and heart, even a selective agonist will activate both to a certain degree. A goal of pharmaceutical chemistry is the development of agonists which are as nearly specific as possible because unselectivity can be a source of side effects.

The prior art makes no prediction about receptor selectivity of adenosine analogs which contain, in the same molecule, the recognition groups which confer specificity for $R_a$ and $R_i$ receptors.

General Formula 1

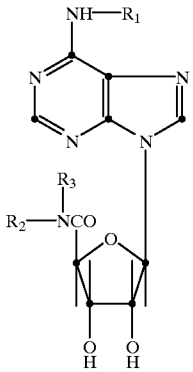

Compound 1 $R_1 = R_3 = H$ $R_2$ = ETHYL
Compound 2 $R_1 = R_3 = R_3 = H$
Compound 3 $R_1 = R_3 = H$ $R_2$ = CYCLOPROPYL-
Compound 4 $R_1 = R_3 = H$ $R_2 = CH_3$-
Compound 5 $R_1 = H$ $R_2 = R_3 = CH_3$
Compound 6 $R_1 = CH_3$ $R_3 = R_2$ = ETHYL
Compound 7 $R_1 = CH_3$ $R_3 = H$ $R_2$ = BUTYL
Compound 8 $R_1 = R_3 = H$ $R_2$ = BUTYL
Compound 15 $R_1 = R_2$ = ETHYL $R_3 = H$
Compound 16 $R_1$ = PROPYL $R_2$ = ETHYL $R_3 = H$ General Formula 2

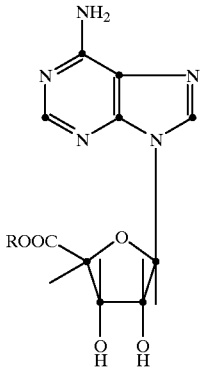

Compound 9 R = H
Compound 10 R = $CH_3$
Compound 11 R = ETHYL
Compound 12 R = n-PROPL
Compound 13 R = i-PROPYL
Compound 14 R = 2-BUTYL Many of the known adenosine derivatives, including the above-noted N-6 substituted and the 5'-carboxamide derivatives are less than satisfactory as cardiovascular or antihypertensive drugs for animal and human use. This is either because of low activity, short duration of the desired activity, undue toxicity or undesirable side effects. Undesirable side effects of cardiovascularly active adenosine analogs often include cardiac depression.

In light of the foregoing, the pharmaceutical industry is still striving to obtain adenosine analogs having high cardiovascular and hypotensive potency coupled with other optimal physiological characteristics, such as relatively long duration of the desired activity, low toxicity and minimal side effects. The compounds of the present invention constitute a step in this direction.

SUMMARY OF THE INVENTION

It is an object of the present invention to provide adenosine analogs which have potent and prolonged cardiovascular activity in mammals and humans, coupled with relatively low toxicity and minimal side effects.

It is another object of the present invention to provide adenosine analogs which have potent or prolonged antihypertensive activity in mammals and humans, coupled with relatively low toxicity and minimal side effects.

It is still another object of the present invention to provide a relatively efficient synthetic process for the preparation of the adenosine derivatives which meet the above-noted objectives.

The foregoing and other objects and advantages are attained by compounds of the General Formula 3, wherein $R_1$ represents secondary alkyl; hydroxy, lower alkoxy or halogen substituted secondary alkyl; aralkyl; aralkyl substituted in the aromatic nucleus with hydroxy, halogen, lower alkoxy or lower alkyl groups; cycloalkyl; hydroxy, lower alkoxy, lower alkyl or halogen substituted cycloalkyl; para-substituted phenyl; heteroaryl substituted alkyl; heteroaryl substituted alkyl substituted in the heteroaryl nucleus with hydroxy, halogen, lower alkoxy or lower alkyl groups; norbornyl, and hydroxy, alkyl or halogen substituted norbornyl groups.

The substituent $R_2$ and $R_3$ groups in the compounds of the present invention, as shown in General Formula 3, are hydrogen, or pharmacologically acceptable organic acyl groups, or inorganic acid radicals, such as $NO_2$ groups, which esterify the hydroxyl groups of the ribofuranose moiety. The $R_2$ and $R_3$ groups are preferably of the type which are relatively readily hydrolyzed under physiological conditions. The $R_2$ and $R_3$ substituents need not be identical with one another.

Still further, in the compounds of General Formula 3, the substituent $R_4$ is straight chain lower alkyl having 1–4 carbon atoms; hydroxy, lower alkoxy or halogen substituted straight chain lower alkyl having 1–4 carbon atoms; cyclopropyl; secondary alkyl having 3–6 carbon atoms; hydroxy, lower alkoxy or halogen substituted secondary alkyl having 3–6 carbon atoms; alkenyl having 3 to 6 carbon atoms; aralkyl having 1 to 4 carbons in the alkyl chain; aralkyl having 1 to 4 carbons in the alkyl chain and substituted in the aryl nucleus with hydroxy, halogen, lower alkoxy or lower alkyl groups; heteroarylalkyl having 1 to 4 carbons in the alkyl chain; and heteroarylalkyl having 1 to 4 carbons in the alkyl chain and substituted in the heteroaryl nucleus with hydroxy, halogen, lower alkoxy or lower alkyl groups. $R_5$ is hydrogen, or straight chain lower alkyl having 1 to 4 carbons.

GENERAL FORMULA 3

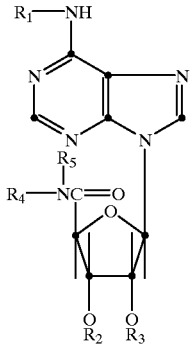

The compounds of the present invention are resistant to enzymatic phosphorylation and to deamination by adenosine deaminase. The compounds exhibit significant cardiovascular activity.

In accordance with a novel process of the invention, the compounds of General Formula 3 are obtained from 2',3'-O-isopropylideneinosine-5'-uronic acid by treatment with a suitable inorganic acid halide, such as thionyl chloride, to yield the intermediate, 6-chloro-9-[2,3-O-isopropylidene-β-D-ribofuranosyl-5-uronic acid chloride]-9H-purine. The intermediate, 6-chloro-9-[2,3-O-isopropylidene-β-D-ribofuranosyl-5-uronic acid chloride]-9H-purine, (or the corresponding bromide, if, for example thionyl bromide is used instead of thionyl chloride) is usually not isolated in a pure state.

The acid chloride moiety of 6-chloro-9-[2,3-O-isopropylidene-β-D-ribofuranosyl-5-uronic acid chloride]-9H-purine (or the acid bromide of the corresponding bromo-analog) is significantly more readily displaced by nucleophilic reagents than the halide group in the 6 position of the purine moiety. Therefore, in accordance with the process of the present invention, 6-chloro-9-[2,3-O-isopropylidene-β-D-ribofuranosyl-5-uronic acid chloride]-9H purine is reacted with a first nucleophilic reagent having the formula $R_4$,$R_5$-NH (General Formula 4) to yield an intermediate substituted carboxamide shown in General Formula 5, wherein the halide is retained in the 6position of the purine moiety.

The intermediate of General Formula 5 is subsequently reacted with a nucleophile having the formula $R_1$- $NH_2$ (General Formula 6) and the isopropylidene blocking group is removed with acid to yield the compounds of the invention (General Formula 3), having free hydroxyl groups in the 2' and 3' positions of the ribofuranose moiety. Instead of the isopropylidene blocking group, other acid stable blocking groups can also be used to protect the 2'—OH and 3'—OH groups of the ribofuranose moiety during the step of treatment with the inorganic acid halide.

The groups $R_1$, $R_4$ and $R_5$ in General Formulae 4–6 are defined the same as in General Formula 3.

GENERAL FORMULA 4

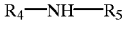

GENERAL FORMULA 6

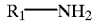

-continued

GENERAL FORMULA 5

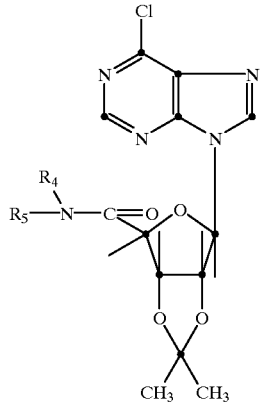

DETAILED DESCRIPTION OF THE INVENTION

Certain derivatives of 5'-carboxamidoadenosine wherein both the amino nitrogen (N-6) of the purine moiety and the amino nitrogen of the 5'-carboxamido moiety are substituted, have been found, in accordance with the present invention, to possess significant cardiovascular and/or anti-hypertensive activity. The compounds of the invention have the composition characterized by General Formula 3. The substituent $R_1$, $R_2$, $R_3$, $R_4$ and $R_5$ groups are defined above in the summary description of the present invention.

A preferred subclass of the compounds of the present invention consists of N-6 substituted derivatives of 5'-N-ethylcarboxamidoadenosine shown in General Formula 7, wherein the $R_1$ substituents of the N-6 amino nitrogen comprise: secondary alkyl; hydroxy, lower alkoxy or halogen substituted secondary alkyl; aralkyl; aralkyl substituted in the aromatic nucleus with hydroxy, halogen, lower alkoxy or lower alkyl groups; cycloalkyl; hydroxy, lower alkoxy, lower alkyl or halogen substituted cycloalkyl; para-substituted phenyl; heteroaryl substituted alkyl; heteroaryl substituted alkyl substituted in the heteroaryl nucleus with hydroxy, halogen, lower alkoxy or lower alkyl groups.

The $R_2$ and $R_3$ substituent groups on the 2' and 3' positions of the ribofuranose moiety are hydrogen, or pharmaceutically acceptable acyl groups, such as acetyl, propionyl, butyryl and benzoyl groups. Especially preferred in this regard, are those acyl groups which are relatively readily split off the ribofuranose moiety under physiological conditions. The $R_2$ and $R_3$ substituent groups can also represent inorganic acid radicals, such as $NO_2$ groups, which esterify the hydroxyl groups of the ribofuranose moiety.

The $R_4$ substituent in the foregoing subclass of compounds shown in General Formula 7, is hydrogen, methyl or ethyl.

Another preferred subclass of the compounds of the present invention consists of derivatives of 5'-carboxamidoadenosine, compounds of General Formula 8, wherein both the N-6 and 5'-carboxamido nitrogens are monosubstituted with the substituents $R_1$ and $R_4$ respectively, and where the $R_2$ and $R_3$ substituents are defined the same as for the compounds of General Formula 7.

In this preferred subclass of compounds, shown in General Formula 8, the $R_1$ substituents are: secondary alkyl; hydroxy, lower alkoxy or halogen substituted secondary alkyl; aralkyl; aralkyl substituted in the aromatic nucleus with hydroxy, halogen, lower alkoxy or lower alkyl groups; cycloalkyl; hydroxy, lower alkoxy, lower alkyl or halogen substituted cycloalkyl; para-substituted phenyl; heteroaryl substituted alkyl; heteroaryl substituted alkyl substituted in the heteroaryl nucleus with hydroxy, halogen, lower alkoxy or lower alkyl groups.

The substituents $R_4$ of the preferred subclass shown in General Formula 8 are: straight chain lower alkyl having 1–4 carbon atoms; hydroxy, lower alkoxy or halogen substituted straight chain lower alkyl having 1–4 carbon atoms; cyclopropyl; secondary alkyl having 3–6 carbon atoms; hydroxy, lower alkoxy or halogen substituted secondary alkyl having 3–6 carbon atoms; alkenyl having 3 to 6 carbon atoms.

Specific examples of preferred compounds of this subclass (General Formula 8) are those where the $R_1$ (N-6) and $R_4$ (5'-carboxamido) substituents are as follows, with $R_2$ and $R_3$ being hydrogen:

Compound 17: $R_1$ is 3-pentyl, $R_4$ is ethyl;
Compound 18: $R_1$ is cyclohexyl, $R_4$ is ethyl;
Compound 19: $R_1$ is (S)-1-phenyl-2-butyl, $R_4$ is ethyl;
Compound 20: $R_1$ is 4-methoxy-phenyl, $R_4$ is ethyl;
Compound 21: $R_1$ is 2-(3,4,5-trimethoxyphenyl)ethyl, $R_4$ is ethyl;
Compound 22: $R_1$ is 3-phenyl-propyl, $R_4$ is ethyl;
Compound 23: $R_1$ is (R)-1-phenylethyl, $R_4$ is ethyl;
Compound 24: $R_1$ is 2-(2-pyridyl)ethyl, $R_4$ is ethyl;
Compound 25: $R_1$ is (2-chlorophenyl)methyl, $R_4$ is ethyl;
Compound 26: $R_1$ is (2-thienyl)methyl, $R_4$ is ethyl;
Compound 27: $R_1$ is endo-2-norbornyl, $R_4$ is 2-hydroxyethyl;
Compound 28: $R_1$ is 3-pentyl, $R_4$ is methyl;
Compound 29: $R_1$ is 3-pentyl, $R_4$ is isopropyl;
Compound 30: $R_1$ is 3-pentyl, $R_4$ is 3-pentyl;
Compound 31: $R_1$ is 3-pentyl, $R_4$ is allyl;
Compound 32: $R_1$ is 3-pentyl, $R_4$ is (2-methyl)propyl;
Compound 33: $R_1$ is 3-pentyl, $R_4$ is cyclopropyl;
Compound 34: $R_1$ is (R)-1-phenyl-2-propyl, $R_4$ is ethyl;

A preferred subgroup within the subclass shown by General Formula 8 comprise compounds in which the 5'-carboxamido group is ethyl substituted. With reference to General Formula 8, specific examples of compounds of this subgroup are:

Compound 17: $R_1$ is 3-pentyl, $R_4$ is ethyl;
Compound 18: $R_1$ is cyclohexyl, $R_4$ is ethyl;
Compound 19: $R_1$ is (S)-1-phenyl-2-butyl, $R_4$ is ethyl;
Compound 20: $R_1$ is 4-methoxy-phenyl, $R_4$ is ethyl;
Compound 21: $R_1$ is 2-(3,4,5-trimethoxyphenyl)ethyl, $R_4$ is ethyl;
Compound 22: $R_1$ is 3-phenylpropyl, $R_4$ is ethyl;
Compound 23: $R_1$ is (R)-1-phenylethyl, $R_4$ is ethyl;
Compound 24: $R_1$ is 2-(2-pyridyl)ethyl, $R_4$ is ethyl;
Compound 25: $R_1$ is (2-chlorophenyl)methyl, $R_4$ is ethyl;
Compound 26: $R_1$ is (2-thienyl)methyl, $R_4$ is ethyl;
Compound 34: $R_1$ is (R)-1-phenyl-2-propyl, $R_4$ is ethyl;

Another preferred subclass of the cardiovascularly active or anti-hypertensive compounds of the present invention is shown by General Formula 9, where the substituents $R_1$, $R_2$ and $R_3$ signify the same groups as in the compounds of General Formula 8. The 5'-carboxamido substituents groups comprise, in this subclass of compounds, aralkyl having 1 to 4 carbons in the alkyl chain, unsubstituted or substituted in the aryl nucleus with hydroxy, halogen, lower alkoxy or lower alkyl groups; heteroarylalkyl having 1 to 4 carbons in the alkyl chain; and heteroarylalkyl having 1 to 4 carbons in the alkyl chain, unsubstituted or substituted in the heteroaryl nucleus with hydroxy, halogen, lower alkoxy or lower alkyl groups. Thus, in the structure symbolized by General Formula 9, n is an integer having the values of 1 to 4, and Q is an aromatic nucleus, or aromatic heterocycle, and Z is one or more H, hydroxy, halogen, lower alkoxy or lower alkyl.

Specific examples of compounds of the subclass of general formula 9 are:

Compound 35 $R_1$ is 3-pentyl and the 5'-carboxamido substituent is phenylmethyl;
Compound 36 $R_1$ is 3-pentyl and the 5'-carboxamido substituent is 2-methoxyphenylmethyl;
Compound 37 $R_1$ is 3-pentyl and the 5'-carboxamido substituent is 2-thienylmethyl;
Compound 38 $R_1$ is 3-pentyl and the 5'-carboxamido substituent is 2-phenylethyl.

GENERAL FORMULA 7

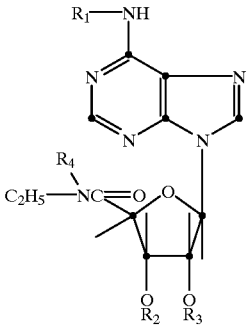

GENERAL FORMULA 8

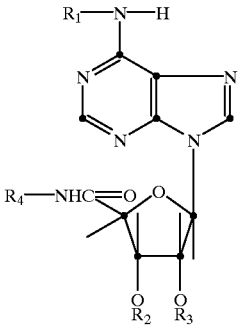

(Compounds 17 through 34)

GENERAL FORMULA 9

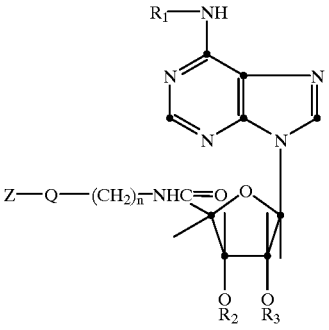

(Compounds 35-38)

Yet another subclass of the compounds of the present invention is shown in General Formula 10. In this subclass of compounds, the N-6 amino group of the purine moiety is substituted with a 3-pentyl group, and the $R_1$ substituent of the 5'-carboxamido group is straight chain lower alkyl having 1–4 carbon atoms; hydroxy, lower alkoxy or halogen substituted straight chain lower alkyl having 1–4 carbon atoms; cyclopropyl; secondary alkyl having 3–6 carbon atoms; hydroxy, lower alkoxy or halogen substituted secondary alkyl having 3–6 carbon atoms; alkenyl having 3 to 6 carbon atoms; aralkyl having 1 to 4 carbons in the alkyl chain; aralkyl having 1 to 4 carbons in the alkyl chain and substituted in the aryl nucleus with hydroxy, halogen, lower alkoxy or lower alkyl groups; heteroarylalkyl having 1 to 4 carbons in the alkyl chain; and heteroarylalkyl having 1 to 4 carbons in the alkyl chain and substituted in the heteroaryl nucleus with hydroxy, halogen, lower alkoxy or lower alkyl groups. The second substituent on the 5'-carboxamido nitrogen, $R_4$, is hydrogen, or straight chain lower alkyl having 1 to 4 carbons. The $R_2$ and $R_3$ substituents on the hydroxyl groups of the ribofuranose moiety are the same as described above in connection with the compounds of General Formulae 7, 8, and 9.

Specific examples of compounds of the subclass of General Formula 10, where the $R_2$ and $R_3$ substituents are hydrogen, are:

Compound 17: $R_1$ is ethyl, $R_4$ is H;
Compound 28: $R_1$ is methyl, $R_4$ is H;
Compound 29: $R_1$ is isopropy, $R_4$ is H;
Compound 30: $R_1$ is 3-pentyl, $R_4$ is H;
Compound 31: $R_1$ is allyl, $R_4$ is H;
Compound 32: $R_1$ is (2-methyl)propyl, $R_4$ is H;
Compound 33: $R_1$ is cyclopropyl, $R_4$ is H;
Compound 35 $R_1$ is phenylmethyl, $R_4$ is H;
Compound 36 $R_1$ is 2-methoxyphenylmethyl, $R_4$ is H;
Compound 37 $R_1$ is 2-thienylmethyl, $R_4$ is H;
Compound 38 $R_1$ is 2-phenylethyl, $R_4$ is H;
Compound 39 $R_1$ is methyl, $R_4$ is methyl;
Compound 40 $R_1$ is n-butyl, $R_4$ is methyl;
Compound 41 $R_1$ is ethyl, $R_4$ is ethyl;

GENERAL FORMULA 10

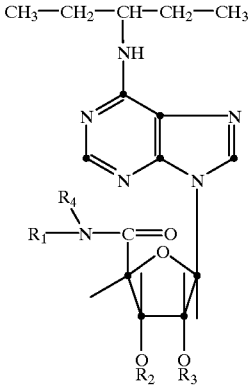

(Compounds 17, 28-33, 35-41)

The physical characteristics and biological activity of specific examples of the compounds of the present invention are noted below together with certain biological activity data. The tests showing the biological activity of the compounds of the present invention are discussed after description of the specific examples.

SPECIFIC EXAMPLES

Ethyl $N^6$-(3-pentyl)adenosine-5'-uronamide, (Compound 17) mp 176–177, uv λmax(ε)=269 nm(18.1×$10^3$) at pH 7. Anal. Calculated for $C_{17}H_{26}N_6O_4$ (378.44): C, 53.96; H, 6.93; N, 22.21. Found: C, 53.82; H, 6.95; N, 22.17. Molar potency ratio (mpr) 3.3±0.25; anti-hypertensive activity at 0.05 mg/kg (22,20,22).

Ethyl $N^6$-cyclohexyladenosine-5'-uronamide, (Compound 18) mp 133–135; uvλmax(ε)=270(18.8×$10^3$) at pH 7. Anal. Calculated for $C_{18}H_{26}N_6O_4$ (382.38): C, 55.37; H, 6.71; N, 21.52. Found: C, 55.34; H, 6.86; N, 21.42. Molar potency ratio (mpr) 1.5±0.24; anti-hypertensive activity at 0.1 mg/kg (13,17,15).

Ethyl $N^6$-(S)-1-phenyl-2-butyladenosine-5'-uronamide, (Compound 19) mp 177–179; uv λmax(ε)270 nm(19.2×$10^3$) at pH 7; $\alpha_D^{25}$=+27 c=1 in 95% ETOH. Anal. Calculated for $C_{22}H_{28}N_6O_4$ (440.51): C, 59.99; H, 6.41; N, 19.08. Found: C, 59.89; H, 6.37; N, 19.06. Anti-hypertensive activity at 0.1 mg/kg (12,14,12).

Ethyl $N^6$-4-methoxyphenyladenosine-5'-uronamide, (Compound 20) mp 189–190; uv λmax(ε)287 nm(19.4×$10^3$) at pH 7; Anal. Calculated for $C_{19}H_{22}N_6O_4$ (414.42): C, 55.07; H, 5.35; N, 20.28. Found: C, 55.16; H, 5.45; N, 20.23. Anti-hypertensive activity at 10 mg/kg (40,47,52)+

Ethyl $N^6$-2-(3,4,5-trimethoxyphenyl)ethyladenosine-5'-uronamide, (Compound 21) mp 154–155; uvλmax(ε)270.5 nm(15.7×$10^3$) at pH 7; Anal. Calculated for $C_{23}H_{30}N_6O_7$ (502.53): C, 54.97; H, 6.02; N, 16.72. Found: C, 55.14; H, 6.13; N, 16.71. Anti-hypertensive activity at 10 mg/kg (18,0,8)+

Ethyl $N^6$-3-phenylpropyladenosine-5'-uronamide, (Compound 22) mp 153–156; uv λmax(ε)268 nm(17.6×$10^3$) at pH 7; Anal. Calculated for $C_{21}H_{26}N_6O_4$ (426.48): C, 59.14; H, 6.15; N, 19.71. Found: C, 59.24; H, 5.91; N, 19.85. Anti-hypertensive activity at 10 mg/kg (39,40,39).+

Ethyl $N^6$-(R)-1-phenyl-ethyladenosine-5'-uronamide, (Compound 23) mp 144–147; uv λmax(ε)270 nm(19.9×$10^3$) at pH 7; Anal. Calculated for $C_{20}H_{24}N_6O_4$ (412.45): C, 58.24; H, 5.87; N, 20.06. Found: C, 58.26; H, 6.00; N, 20.22. Anti-hypertensive activity at 1 mg/kg, rio detectable signal of blood pressure.

Ethyl $N^6$-2-(2-pyridyl)ethyladenosine-5'-uronamide, (Compound 24) mp 126–127; uv λmax(ε)268.5 nm(20.5×$10^3$) at pH 7; Anal. Calculated for $C_{19}H_{23}N_7O_4$ (413.44): C, 55.20; H, 5.61; N, 23.71. Found: C, 55.38; H, 5.82; N, 23.87. Anti-hypertensive activity at 10 mg/kg (31,16,21).+

Ethyl $N^6$-(2-chlorophenyl)methyladenosine-5'-uronamide, (Compound 25) mp 134–136; uv λmax(ε)267.5 nm(19.4×$10^3$) at pH 7; Anal. Calculated for $C_{19}H_{21}ClN_6O_4.4.H_2O$ (450.89): C, 50.61; H, 5.14; N, 18.64. Found: C, 50.85; H, 5.04; N, 18.49. Anti-hypertensive activity at 5 mg/kg, no detectable signal of blood pressure.

Ethyl $N^6$-2-thienylmethyladenosine-5'-uronamide, (Compound 26) mp 164–165; uv λmax(ε)268.5 nm(21.2×$10^3$) at pH 7. Anal. Calculated for $C_{17}H_{20}N_6O_4S$ (404.45): C, 50.49; H, 4.98; N, 20.78. Found: C, 50.46; H, 5.21; N, 20.81. Anti-hypertensive activity at 5 mg/kg (22,32,29)+

2-Hydroxyethyl $N^6$-endo-2-norbornyladenosine-5'-uronamide, (Compound 27) mp 132–134; uvλmax(ε)270.5 nm(18.5×$10^3$) at pH 7; Anal. Calculated for $C_{19}H_{26}N_6O_5.H_2O$ (420.48): C, 54.27; H, 6.71; N, 19.99. Found: C, 54.22; H, 6.66; N, 19.90. Anti-hypertensive activity at 1 mg/kg (8,33,36)*

Methyl $N^6$-3-pentyladenosine-5'-uronamide, (Compound 28) mp 126–128; uv λmax(ε)269 nm(18.5×$10^3$) at pH 7; Anal. Calculated for $C_{16}H_{24}N_6O_4$ (364.41): C, 52.74; H, 6.64; N, 23.06. Found: C, 52.66; H, 6.70; N, 23.16. Anti-hypertensive activity at 0.5 mg/kg (14,17,17).

Isopropyl $N^6$ -3-pentyladenosine-5'-uronamide, (Compound 29) mp 191–193; uv λmax(ε)269 nm(18.3×$10^3$) at pH 7; Anal. Calculated for $C_{18}H_{28}N_6O_4$ (392..46): C, 55.09; H, 7.19; N, 21.41. Found: C, 55.03; H, 7.37; N, 21.27. Anti-hypertensive activity at 0.5 mg/kg (11,24,18).

3-Pentyl $N^6$-3-pentyladenosine-5'-uronamide, (Compound 30) mp 211–212; uv λmax(ε)270 nm(17.9×$10^3$) at pH 7; Anal. Calculated for $C_{20}H_{32}N_6O_4$ (420.52): C, 57.13; H, 7.67; N, 19.98. Found: C, 57.35; H, 7.76; N, 19.81. Anti-hypertensive activity at 20 mg/kg (6,21,17).

Allyl-$N^6$-3-pentyladenosine-5'-uronamide, (Compound 31) mp 169–170; uv λmax(ε)269 nm(19.2×$10^3$) at pH 7; Anal. Calculated for $C_{18}H_{26}N_6O_4$ (390.45): C, 55.37; H, 6.71; N, 21.52. Found: C, 55.24; H, 6.97; N, 21.31. Anti-hypertensive activity at 2.5 mg/kg (15,15,20).

(2-Methyl)-propyl $N^6$-3-pentyladenosine-5'-uronamide, (Compound 32) mp 206–207; uv λmax(ε)268.5 nm(16.9×$10^3$) at pH 7; Anal. Calculated for $C_{19}H_{30}N_6O_4$ (406.49): C, 56.14; H, 7.44; N, 20.67. Found: C, 56.22; H, 7.46; N, 20.76. Anti-hypertensive activity at 10 mg/kg (15,19,13).

Cyclopropyl $N^6$-3-pentyladenosine-5'-uronamide, (Compound 33) mp 181–183; uv λmax(ε)269 nm(20.0×$10^3$) at pH 7; Anal. Calculated for $C_{18}H_{26}N_6O_4$ (390.45): C, 55.37; H, 6.71; N, 21.52. Found: C, 55.11; H, 6.65; N, 21.66. Anti-hypertensive activity at 0.25 mg/kg (21,21,28), molar potency ratio (mpr) 2.3.

Ethyl $N^6$-(R)-1-phenyl-2-propyladenosine-5'-uronamide, (Compound 34) mp 157–158; uv λmax(ε)=270 nm(18.0×$10^3$) at pH 7. α%hd $D^{25}$=−104.5. Anal. Calculated for $C_{21}H_{26}N_6O_4$ (426.48): C, 59.14; H, 6.15; N, 19.71. Found: C, 58.91; H, 6.10; N, 19.64. Molar potency ratio (mpr) 4.3.±0.60;

Phenylmethyl $N^6$-3-penthyladenosine-5'-uronamide, (Compound 35) mp 174–175; uv λmax(ε)269 nm(17.4×$10^3$) at pH 7; Anal. Calculated for $C_{22}H_{28}N_6O_4$ (440.51): C, 59.99; H, 6.41; N, 19.08. Found: C, 59.76; H, 6.34; N, 19.07. Anti-hypertensive activity at 5 mg/kg (18,26,22).

2-Methoxyphenylmethyl $N^6$-3-pentyladenosine-5'-uronamide, (Compound 36) mp 176–178; uv λmax(ε)269.5 nm(18.9×$10^3$) at pH 7; Anal. Calculated for $C_{23}H_{30}N_6O_5$ (470.53): C, 58.71; H, 6.43; N, 17.86. Found: C, 58.53; H, 6.68; N, 17.65. Anti-hypertensive activity at 10 mg/kg (12,18,18).

2-Thienylmethyl $N^6$-3-pentyladenosine-5'-uronamide, (Compound 37) mp 160–161; uv λmax(ε)237 nm(10.1×$10^3$), 269.0 nm(17.4×$10^3$) at pH 7; Anal. Calculated for $C_{20}H_{26}N_6O_4S$ (446.53): C, 53.80; H, 5.87; N, 18.82. Found: C, 53.62; H, 6.00; N, 19.00. Anti-hypertensive activity at 5 mg/kg (16,16,14).

2-Phenylethyl $N^6$ -3-pentyladenosine-5'-uronamide, (Compound 38) mp 203–204; uv λmax(ε)268.5 nm(18.8×$10^3$) at pH 7; Anal. Calculated for $C_{23}H_{30}N_6O_4$ (453.53): C, 60.78; H, 6.65; N, 18.49. Found: C, 60.88; H, 6.67; N, 18.50. Anti-hypertensive activity at 40 mg/kg (17,13,15).

Dimethyl $N^6$-3-pentyladenosine-5'-uronamide, (Compound 39) mp 168–169; uv λmax(ε)269 nm(18.7×$10^3$) at pH 7; Anal. Calculated for $C_{17}H_{26}N_6O_4$ (378.44): C, 53.96; H, 6.93; N, 22.21. Found: C, 53.71; H, 7.11; N, 22.34. Anti-hypertensive activity at 2.5 mg/kg (25,23,17).

Methyl,n-butyl $N^6$-3-pentyladenosine-5'-uronamide, (Compound 40) mp 139–141; uv λmax(ε)270 nm(19.2×$10^3$) at pH 7; Anal. Calculated for $C_{20}H_{32}N_6O_4$ (420.52): C, 57.13; H, 7.67; N, 19.98. Found: C, 57.26; H, 7.50; N, 19.92. Anti-hypertensive activity at 1 mg/kg (31,21,27).

Diethyl $N^6$-3-pentyladenosine-5'-uronamide, (Compound 41) mp 148–150; uv λmax(ε)269 nm(19.0×$10^3$) at pH 7; Anal. Calculated for $C_{17}H_{30}N_6O_4$ (406.49): C, 56.14; H, 7.44; N, 20.67. Found: C, 56.42; H, 7.29; N, 20.67. Anti-hypertensive activity at 1 mg/kg (10,13,11).

Dimethyl $N^6$-2-(2-chlorophenyl)-ethyladenosine-5'-uronamide, (Compound 42) mp 129–131; uv λmax(ε)268.5 nm(20.2×$10^3$) at pH 7; Anal. Calculated for $C_{20}H_{23}ClN_6O_4$ (446.90): C, 53.75; H, 5.19; N, 18.81. Found: C, 53.91; H, 5.37; N, 18.59. Anti-hypertensive activity at 5 mg/kg (20, 19,13)+.

PROCESS FOR MAKING THE COMPOUNDS OF THE INVENTION

The compounds of the present invention are prepared in accordance with a novel process of the invention from a suitably blocked derivative of inosine-5'-uronic acid, such as 2',3'-O-isopropylideneinosine-5'-uronic acid (Compound 43). 2',3'-O-isopropylideneinosine-5'-uronic acid (Compound 43) is readily obtained from inosine by treatment with acetone to block the 2'- and 3'- hydroxy groups of the ribofuranose moiety, followed by oxidation with chromic acid, in accordance with the published procedure of R. R. Schmidt and H. J. Fritz, Chemische Berichte., 103, 1867 (1970).

2',3'-O-isopropylideneinosine-5'-uronic acid (Compound 43) is treated in accordance with the process of the present invention, with a suitable inorganic acid halide, such as thionyl chloride, to convert, in the same reaction step, the uronic acid moiety into a uronic acid halide and to introduce a halogen substitutent into the 6 position of the purine moiety. In this regard it is noted that the blocking groups of the 2' and 3' hydroxyl groups must be capable of withstanding the conditions of this reaction, which is advantageously conducted in neutral solvents, such as chloroform, in the presence of dimethylformamide or other dialkylamides. The isopropylidene blocking group serves well for this purpose. Nevertheless, other ketal, acetal or even acyl blocking groups are also suitable. Instead of thionyl chloride other inorganic acid halides, such as thionyl bromide, may also be used. The product of the just described first step of the novel reaction sequence is 6-chloro-9-[2,3-O-isopropylidene-β-D-ribofuranosyl 5-uronic acid chloride]-9H-purine (Compound 44).

The reaction sequence leading to the compounds of the present invention, using the example of 6-chloro-9-[2,3-O-isopropylidene-β-D-ribofuranosyl 5-uronic acid chloride)-9H-purine (Compound 44) as the important intermediate, is shown in Reaction Scheme 1.

REACTION SCHEME 1

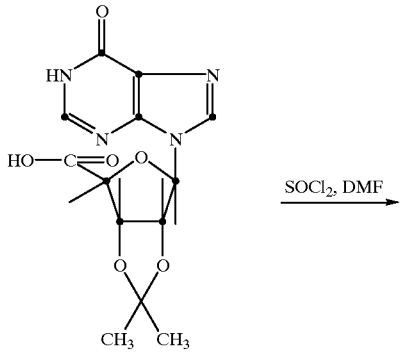

Compound 43

-continued

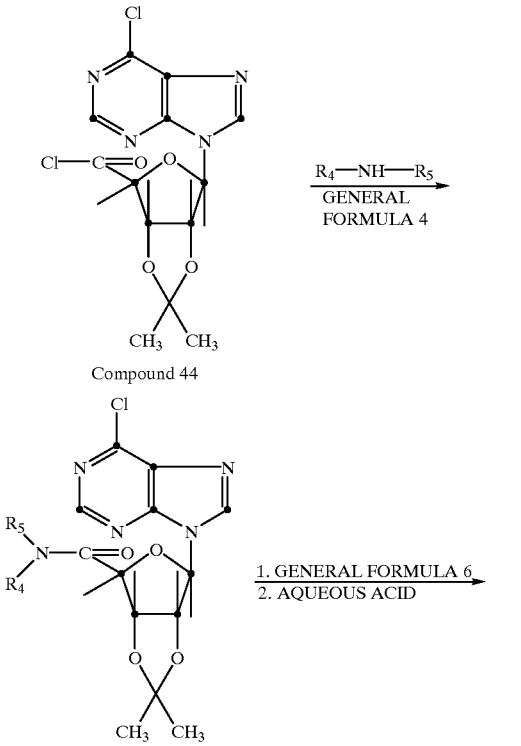

6-chloro-9-[2,3-O-isopropylidene-β-D-ribofuranosyl-5-uronic acid chloride]-9H-purine (Compound 44) is preferably not isolated in a pure state. Rather, it is reacted with an amine of the General Formula 4 to displace the halide of the uronic acid moiety and to provide compounds of the General Formula 5, wherein the halogen in the 6 position of the purine nucleus is retained. This selective displacement of the "acid chloride" group is readily conducted in neutral solvents, such as chloroform, preferably at low temperature.

The intermediates of General Formula 5, may be isolated in a purified state. They are subsequently reacted with a nucleophilic amine of General Formula 6 in a suitable solvent such as ethyl alcohol, to displace the halogen substituent in the 6 position of the purine nucleus. The displacement reaction is preferably conducted in the presence of an acid acceptor, such as triethyl amine. The blocking groups of the 2' and 3' hydroxyls of the ribofuranose moiety are thereafter removed to provide the compounds of the invention (General Formula 3). Removal of the isopropylidene blocking groups is affected, for example, by heating with aqueous hydrochloric acid. These steps are illustrated in the continuation of Reaction Scheme 1. In the formulae shown in Reaction Scheme 1, the definition of the substituent R groups is the same as was given above in connection with the respective general formulae.

Specific examples of the steps of the novel process of the present invention for the preparation of ethyl $N^6$-(3-pentyl) adenosine-5'-uronamide (Compound 17) and of N,N-dimethyl $N^6$-(3-pentyl)adenosine-5'-uronamide (Compound 39) are given below.

Actually, the invention of the herein disclosed novel process is broader than the preparation of the herein disclosed compounds having beneficial cardiovascular or anti-hypertensive properties. In a broad sense, a multitude of N-6 and 5'-N substituted adenosine 5'-uronamides can be synthesized in accordance with the process of the present invention. The compounds which are obtainable by the process of the present invention include, in addition to the compounds described above, those compounds wherein the carboxamido nitrogen is mono or di substituted with alkyl, alkenyl, cycloalkyl, aralkyl, and heterocyclyl groups. The carboxamido nitrogen (5'-N) can also be a member of a saturated heterocyclic ring such as a piperidine or morpholine ring.

An alternative process for the preparation of at least some of the compounds of the present invention comprises the steps of oxidizing N-6 substituted adenosine derivatives which are suitably protected (for example by isopropylidene or benzyl groups) on the 2' and 3' hydroxyl groups. The step of oxidation is conducted in analogy to the procedure published by R. R. Schmidt and H. J. Fritz in Chemische Berichte, 103, 1867 (1970). The N-6 substituted adenosine derivatives can be obtained by reaction of 6-chloro-β-D-ribofuranosyl-9H-purine with the suitable amine.

The resulting uronic acid is then converted to the corresponding acid halide by treatment, for example, with thionyl chloride, in analogy to the process which was described above. The resulting uronic acid halide is thereafter reacted with a primary amine bearing the desired $R_4$ and $R_5$ substituents. After removal of the protecting groups from the ribofuranosyl moiety, the compounds of the present invention are obtained.

6-Chloro-9-[2,3-O-isopropylidene-5-ethylcarboxamido-β-D-ribofuranosyl]-9H-purine (Compound 45).

A mixture of 2',3'-O-isopropylideneinosine-5'-uronic acid (6.5 g, 20 mmols), thionyl chloride (4 ml, 53.3 mmols), dry dimethylformamide (1.5 ml, 40 mmols) and dry chloroform (250 ml) was refluxed for 4 to 5 hours. The chloroform was removed in vacuo to give a syrup. The syrup was dissolved in dry chloroform (80 ml), and the resulting solution was added to a mixture of ethylamine (14 mi) and dry chloroform (150 ml) at 10° C. The mixture was stirred for one hour at 10° C., and then poured into cold water (300 ml). The resulting organic layer was separated and washed in succession with aqueous hydrochloric acid (10%, 2×200 ml), aqueous sodium bicarbonate solution (saturated, 1×200 ml) and water (1×100 ml), and dried over magnesium sulfate. The chloroform solvent was removed in vacuo to give 6.3 g (85% yield) of a slightly yellow solid. The product is usable in the subsequent reaction steps without further purification.

Ethyl $N^6$-(3-pentyl)adenosine-5'-uronamide, (Compound 17)

A mixture of 6-Chloro-9-[2,3-O-isopropylidene-5-ethylcarboxamido-β-D-ribofuranosyl]-9H-purine (Compound 45) (6.3 g, 17.1 mmols), 3-pentylamine (1.6 g, 18.4 mmols), triethylamine (4.7 ml, 34 mmols) and absolute ethanol (200 ml) was refluxed for about 48 hours, or until thin layer chromatography indicated complete reaction. The ethanol was removed in vacuo and the product purified by chromatography on a silica gel column eluted with chloroform/acetone 16:1. Evaporation of fractions containing product yielded a syrup which was heated for 1.5 hours with aqueous hydrochloric acid (1.0 N, 100 ml) at 70° C. Upon cooling it yielded Compound 17 as white crystals. Recrystallization from ethanol yielded white needles, (4.5 g, 70% yield). The physical characteristics and analytical data of Compound 17 were described above.

Dimethyl $N^6$-(3-pentyl)adenosine-5'-uronamide (Compound 39) from 2',3'-O-isopropylideneinosine-5'-uronic acid (Compound 43)

A mixture of 2',3'-O-isopropylideneinosine-5'-uronic acid (5.0 g; 15.5 mmols) thionyl chloride (2.5 ml; 33.3 mmols) dry dimethylformamide (1.25 ml; 18.1 mmols) and dry chloroform (170 ml) was refluxed for 5 hours. The solvents were removed in vacuo to give a syrup. The syrup was dissolved in dry chloroform (50 ml) and the resulting solution was added to a mixture of dimethylamine (20 ml, 302 mmols) and dry chloroform (150 ml) at 10° C. The mixture was stirred for 15 minutes after the addition was complete, and thereafter poured into cold water (300 ml). The organic phase was separated and washed successively with water (1×100 ml), 10% aqueous hydrochloric acid solution (2×100 ml), saturated aqueous sodium bicarbonate solution, and was thereafter dried with anhydrous magnesium sulfate. The chloroform solvent was removed in vacuo to give a syrup. The syrup was refluxed for 48 hours (or until thin layer chromatography indicated complete reaction) with 3-pentylamine (2.3 ml; 20 mmols), triethylamine (2.8 ml, 20 mmols) and anhydrous ethanol (100 ml). The solvent and volatile reagents were removed in vacuo to give a syrup (blocked nucleoside). The blocked (isopropylidine) nucleoside was purified by C-18 high performance low pressure liquid chromatography (HPLPLC), methanol-water (70%) being used as the eluent. The solvent was removed in vacuo from the appropriate fractions, to yield a light yellow solid which was thereafter heated at 70° C. for 1.5 hours in 2N aqueous hydrochloric acid (100 ml). Cooling and neutralization with solid sodium bicarbonate yielded Compound 39 as a white syrup, which was crystallized from methanol/water to give 4.0 g (68%) of colorless needles. The physical characteristics and analytical data of Compound 39 were described above.

BIOLOGICAL ACTIVITY AND PHARMACOLOGICAL PROPERTIES

The cardiovascular and anti-hypertensive activities of the compounds of the present invention were determined in bioassays conducted on dogs and spontaneously hypertensive rats.

More particularly, in one type of assay in which the activity of the compounds of the present invention was determined, the compounds to be tested are infused intracoronarily into either open-chest anesthetized or conscious dogs. Adenosine has a demonstrable coronary dilator effect under these conditions. The concentration of the test compound in coronary plasma which causes half-maximal vasodilation is designated ED-50.

More specifically, ED-50 is determined in the following manner. Late diastolic coronary conductance (LDCC) of the experimental dog is monitored through suitable instrumentation. Late diastolic coronary conductance is measured at maximum coronary vasodilation (peak reactive hyperemid), and is designated $LDCC_{max}$. Late diastolic coronary conductance is also measured at basal coronary vasodilation, and is designated $LDCC_0$.

The difference between instantaneously measured late diastolic coronary conductance (LDCC) and basal late diastolic coronary conductance ($LDCC_0$) is expressed as a fraction of the difference between maximum late diastolic coronary conductance ($LDCC_{max}$) and basal late diastolic coronary conductance ($LDCC_0$). Thus, LDCC is defined by Equation I.

$$LDCC = \frac{LDCC - LDCC_0}{LDCC_{max} - LDCC_0} \qquad \text{EQUATION I}$$

As the concentration of the test compound is varied, and the corresponding LDCC is obtained through measurements and the above-summarized calculations, data of an "LDCC versus concentration" function or plot are obtained.

ED-50 is derived from these data by log-logit transformation of the "LDCC versus concentration" plot; namely by solving the linear regression of logit (LDCC) on log (concentration) for LDCC=0.5.

When ED-50 of a tested compound is compared to ED-50 of adenosine in the same dog, as is set forth in EQUATION II, then the resulting molar potency ratio (mpr) provides good comparison of the cardiovascular activity of the tested compound with cardivascular activity of other compounds in the same or other experimental dogs. Thus, molar potency ratio (mpr) is a useful measure of the cardiovascular vasodilatory effect, and hence of the utility of the tested compounds. The greater the vasodilatory effect of a tested compound, the larger the corresponding molar potency ratio (mpr).

$$MPR = \frac{ED - 50(\text{adenosine})}{ED_{50}(\text{tested compound})} \qquad \text{EQUATION II}$$

For a more detailed description of the bioassay used for determining molar potency ratios, reference is made to an article written by Olsson et al., and titled "Coronary Vasoactivity of Adenosine in the Conscious Dog", Circulation Research, 45, 468 (1979).

Molar potency ratios of the specific examples of the compounds of the present invention are listed above next to the detailed description of the specific compounds. These data demonstrate that the compounds are cardiovascularly active.

In another assay for the anti-hypertensive activity of the compounds of the invention, blood pressure of unanesthetized, unheated spontaneously hypertensive rats (SHR) is measured indirectly (through a tail cuff) usually at 2, 4, and 6 hours after oral administration of a single dose of the compounds of the invention. Reduction in mean blood pressure by more than ten per cent (10%) indicates anti-hypertensive activity. The test itself, is well established in the art and need not described here in further detail.

The data obtained in the hypertensive rat (SHR) assay are indicated next to the description of the compounds. In the data, the percentage reduction of blood pressure in 2, 4 and 6 hours after the single oral dose is indicated in parentheses. A * sign after the data shows that the measured reduction of blood pressure occurred 1, 2, and 3 hours after the oral dose; a + sign indicates that the measured reduction occurred in 1, 2 and 2.5 hours after the oral dose. The data demonstrate the anti-hypertensive activity of the compounds of the invention.

An assay for the affinity of some of the compounds of the present invention for $R_a$ receptors employs a modification of the radioligand displacement method described by Fox and Kurpis in The Journal of Biological Chemistry, Volume 258 pages 6952–55 (1983). Briefly, this method comprises the steps of incubating [$^3$H]NECA and the analogs to be tested, with human placenta membrane particles, a source of $R_a$ receptors. The particles are then filtered, washed with a buffer to remove unbound ligand and then the amount of bound radioligand is measured. By varying the concentration of the competing analog one may estimate an index of binding affinity, IC-50, the concentration of which causes half-maximum displacement of [$^3$H]NECA. Using [$^3$H] NECA in this assay instead of [$^3$H]-2-chloroadenosine is a modification of the original method.

The compounds of the present invention were found to compete weakly, or not at all, with [$^3$H]ethyladenosine-5'-uronamide at $R_a$ receptor sites of human placenta.

The foregoing indicates that the compounds of the present invention are selective to $R_a$ receptors of the cardiovascular system. Such selectivity would not be expected on the basis of prevailing prior art theory.

Further advantages of the compounds of the present invention include their inability to undergo phosphorylation in the 5'-position, and their stability to acid. Therefore, the therapeutic effect of the compounds of the present invention is unlikely to be eliminated by the action of phosphorylating enzymes, and the compounds are unlikely to be incorporated into DNA or RNA. As is known, incorporation into RNA or DNA is likely to cause teratogenic, mutagenic or carcinogenic effects.

Moreover, because the compounds of the present invention are stable to acid (they survive heating with 1N aqueous HCl for 1.5 hour at 70° C.) they are capable of surviving the acidic conditions prevailing in the stomach. Therefore, they are suitable as drugs for oral administration to humans and animals.

Various modifications of the herein disclosed invention, in terms of structural modifications of the invented compounds and also in terms of making or using the same, may become readily apparent to those skilled in the art in light of the above disclosure. For example the compounds of the present invention may be administered as pharmaceutically acceptable salts.

Inasmuch as the compounds of the present invention are useful as cardiac vasodilators, cardivascular, and particularly as anti-hypertensive agents in mammals, domestic animals and humans, various modes of administering the compounds will be apparent to a person having average skill in the art. Such modes of administering the compounds include oral and topical administration, and intravenous infusion. One having average skill in the art may readily prepare suitable formulations for the above-mentioned and other modes of administering the compounds of the invention.

In light of the foregoing, the scope of the present invention should be interpreted solely from the following claims, as such claims are read in light of the disclosure.

What is claimed is:

1. [Compounds] *A compound* of the formula:

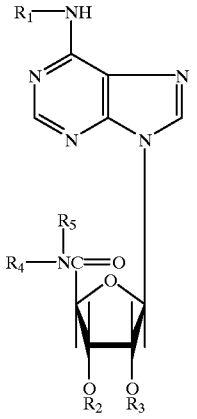

wherein:

$R_1$ represents [secondary alkyl having from 3 to 10 carbons,] phenylalkyl, having from 1 to 7 carbons in the alkyl chain; mono- to penta-alkoxy phenylalkyl wherein said alkoxy contains from 1 to 3 carbons and said alkyl contains from 1 to 7 carbons; monohalophenylalkyl wherein said alkyl contains from 1 to 4 carbons; cycloalkyl wherein the ring contains from 3 to 8 carbons; bicycloalkyl wherein the rings together contain from 7 to 10 carbons; thienylalkyl wherein said alkyl contains from one to four carbons; pyridylalkyl wherein said alkyl contains from one to four carbons;

$R_2$ and $R_3$ are hydrogen;

$R_4$ is alkyl having 1 to 7 carbon atoms; or hydroxyalkyl which contains from 1 to 4 carbons; or secondary alkyl which contains from 3–8 carbons; or allylic alkenyl which contains from 3 to 7 carbons; or cycloalkyl wherein the ring contains from 3 to 7 carbons; or phenylalkyl wherein said alkyl contains from 1 to 4 carbons; or monoalkoxy phenylalkyl wherein said alkoxy and said alkyl each contain from 1 to 4 carbons; or thienylalkyl wherein said alkyl contains from 1 to 4 carbons; and $R_5$ is hydrogen, or straight chain lower alkyl having 1 to 4 carbons.

2. [Compounds] *The compound* of claim 1 wherein $R_4$ is methyl or ethyl.

3. [Compounds] *The compound* of claim 1 wherein $R_1$ is endo-2-norbornyl, $R_4$ is 2-hydroxyethyl and $R_5$ is hydrogen.

4. [Compounds] *The compound* of claim 1 wherein $R_4$ is ethyl and $R_5$ is hydrogen.

5. [Compounds] *The compound* of claim 4 wherein $R_1$ is cyclohexyl.

6. [Compounds] *The compound* of claim 4 wherein $R_1$ is (S)-1-phenyl-2-butyl.

7. [Compounds] *The compound* of claim 4 wherein $R_1$ is 4-methoxyphenyl.

8. [Compounds] *The compound* of claim 4 wherein $R_1$ is 2-(3,4,5-trimethoxyphenyl)-ethyl.

9. [Compounds] *The compound* of claim 4 wherein $R_1$ is 3-phenylpropyl.

10. [Compounds] *The compound* of claim 4 wherein $R_1$ is (R)-1-phenyl-ethyl.

11. [Compounds] *The compound* of claim 4 wherein $R_1$ is 2-(2-pyridyl)ethyl.

12. [Compounds] *The compound* of claim 4 wherein $R_1$ is (2-chloro-phenyl)-methyl.

13. [Compounds] *The compound* of claim 4 wherein $R_1$ is (2-thienyl)methyl.

14. [Compounds] *The compound* of claim 4 wherein $R_1$ is (R)-1-phenyl-2-propyl.

15. The [compounds] *compound* of claim 1 wherein $R_4$ is Z—Q—$(CH_2)_n$ wherein n is an integer having the values of 1 to 4; Q is selected from the group consisting of phenyl, *and* thienyl, [or pyridyl,] and Z is [one or more] H[, hydroxy, halogen, alkoxy having from 1 to 4 carbon atoms, or alkyl having from 1 to 7 carbon atoms].

16. [Compounds] *The compound* of claim 1 wherein $R_1$ is *cycloalkyl or bicycloalkyl.*

17. [Compounds] *The compound* of claim 16 wherein $R_4$ is ethyl, *and* $R_5$ is H.

18. [Compounds] *The compound* of claim 16 wherein $R_4$ is methyl, *and* $R_5$ is H.

19. [Compounds] *The compound* of claim 16 wherein $R_4$ is isopropyl, *and* $R_5$ is H.

20. [Compounds] *The compound* of claim 16 wherein $R_4$ is 3-pentyl, *and* $R_5$ is H.

21. [Compounds] *The compound* of claim 16 wherein $R_4$ is allyl, *and* $R_5$ is H.

22. [Compounds] *The compound* of claim 16 wherein $R_4$ is (2-methyl) propyl, *and* $R_5$ is H.

23. [Compounds] *The compound* of claim 16 wherein $R_4$ is cyclopropyl, *and* $R_5$ is H.

24. [Compounds] *The compound* of claim 16 wherein $R_4$ is phenylmethyl, *and* $R_5$ is H.

25. [Compounds] *The compound* of claim 16 wherein $R_4$ is 2-methoxyphenylmethyl, *and* $R_5$ is H.

26. [Compounds] *The compound* of claim 16 wherein $R_4$ is 2-thienylmethyl, *and* $R_5$ is H.

27. [Compounds] *The compound* of claim 16 wherein $R_4$ is 2-phenylmethyl, *and* $R_5$ is H.

28. [Compounds] *The compound* of claim 16 wherein $R_4$ is methyl, *and* $R_5$ is methyl.

29. [Compounds] *The compound* of claim 16 wherein $R_4$ is n-butyl, *and* $R_5$ is methyl.

30. [Compounds] *The compound* of claim 16 wherein $R_4$ is ethyl, *and* $R_5$ is ethyl.

31. [Compounds] *The compound* of claim 1 wherein $R_1$ is

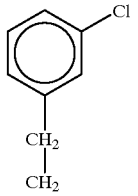

and $R_4$ and $R_5$ are methyl.

32. A pharmaceutical composition comprising a compound of claim 1 in admixture with one or more pharmaceutically acceptable carriers.

33. A method of administering to humans or animals of the mammalian species a vasodilator or anti-hypertensive compound in a therapeutically effective does to achieve a vasodilatory or anti-hypertensive effect, the compound having the formula

14

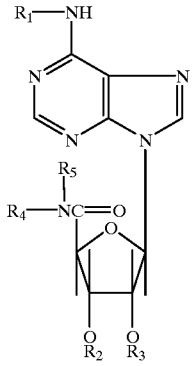

wherein:

$R_1$ represents secondary alkyl having from 3 to 10 carbons; phenylalkyl, having from one to seven carbon atoms in the alkyl chain; mono- to penta-alkoxy phenylalkyl wherein said alkoxy contains from 1 to 3 carbons and said alkyl contains from 1 to 7 carbons; monohalophenylalkyl wherein said alkyl contains from 1 to 4 carbons; cycloalkyl wherein the ring contains from 3 to 8 carbons; bicycloalkyl wherein the rings together contain from 7 to 10 carbons; thienylalkyl wherein said alkyl contains from one to four carbons; pyridylalkyl wherein said alkyl contains from one to four carbons;

$R_2$ and $R_3$ are hydrogen;

$R_4$ is alkyl having 1 to 7 carbon atoms; or hydroxyalkyl which contains from 1 to 4 carbons; or secondary alkyl which contains from 3–8 carbons; or allylic alkenyl which contains from 3 to 7 carbons; or cycloalkyl wherein the ring contains from 3 to 7 carbons; or phenylalkyl wherein said alkyl contains from 1 to 4 carbons; or monoalkoxy phenylalkyl wherein said alkoxy and said alkyl each contain from 1 to 4 carbons; or thienylalkyl wherein said alkyl contains from 1 to 4 carbons; and $R_5$ is hydrogen, or straight chain lower alkyl having 1 to 4 carbons.

34. The method of claim 33 wherein in the formula of the administered compound $R_4$ is ethyl and $R_5$ is hydrogen.

35. The method of claim 33 wherein in the formula of the administered compound $R_1$ is 3-pentyl.

* * * * *

UNITED STATES PATENT AND TRADEMARK OFFICE

CERTIFICATE OF CORRECTION

PATENT NO. : RE 37,045 E
DATED : February 6, 2001
INVENTOR(S) : Olsson et al.

It is certified that error appears in the above-identified patent and that said Letters Patent is hereby corrected as shown below:

Title page,
Item [54], ("Title"), please delete "CARBOXAMIDE" and insert therein -- CARBOXAMIDO --; and please delete "VASODILATOR" and insert therein -- VASODILATORS --.

Column 18,
Line 67, please delete "chloro-phenyl" and insert therein -- chlorophenyl --.

Column 19,
Line 12, after "*bicycloalkyl.*", please insert therein

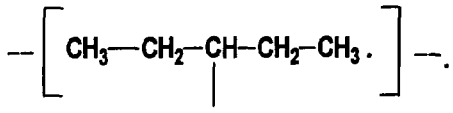

Line 23, please delete "(2-methyl) propyl" and insert therein -- (2-methyl)propyl --.

Column 20,
Line 1, please delete "does" and insert therein -- dose --.

Signed and Sealed this

Eighteenth Day of June, 2002

*Attest:*

*Attesting Officer*

JAMES E. ROGAN
*Director of the United States Patent and Trademark Office*